(12) United States Patent
Huang et al.

(10) Patent No.: US 10,357,217 B2
(45) Date of Patent: Jul. 23, 2019

(54) METHOD FOR POSITRON EMISSION TOMOGRAPHY (PET) IMAGING ANALYSIS FOR CLASSIFYING AND DIAGNOSING OF NEUROLOGICAL DISEASES

(71) Applicant: THE REGENTS OF THE UNIVERSITY OF CALIFORNIA, Oakland, CA (US)

(72) Inventors: Sung-Cheng Huang, Sherman Oaks, CA (US); Koon-Pong Wong, Los Angeles, CA (US); Gary W. Small, Los Angeles, CA (US); Jorge R. Barrio, Agoura Hills, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 6 days.

(21) Appl. No.: 15/787,627

(22) Filed: Oct. 18, 2017

(65) Prior Publication Data

US 2018/0103921 A1    Apr. 19, 2018

Related U.S. Application Data

(60) Provisional application No. 62/409,724, filed on Oct. 18, 2016.

(51) Int. Cl.
*A61B 6/00* (2006.01)
*G06T 7/11* (2017.01)
(Continued)

(52) U.S. Cl.
CPC .......... *A61B 6/5247* (2013.01); *A61B 5/0042* (2013.01); *A61B 5/4064* (2013.01);
(Continued)

(58) Field of Classification Search
CPC ... A61B 6/5247; A61B 6/5217; A61B 5/7275; A61B 5/4088; A61B 5/4064;
(Continued)

(56) References Cited

U.S. PATENT DOCUMENTS 5,510,522 A    4/1996 Satyamurthy et al.
5,861,503 A    1/1999 Barrio et al.
(Continued)

FOREIGN PATENT DOCUMENTS

WO    2005/040337    5/2005

OTHER PUBLICATIONS

Small, Gary W. et al., PET of Brain Amyloid and Tau in Mild Cognitive Impairment, N Engl J Med 355;25, www.nejm.org, Dec. 21, 2006, 2652-2663.
(Continued)

*Primary Examiner* — Sanjay Cattungal
(74) *Attorney, Agent, or Firm* — Vista IP Law Group LLP (57) ABSTRACT

A method of using PET imaging includes using PET images obtained using a radiotracer for the determination of the progressive course of regional brain PET activities for a progressive neurodegenerative disease (e.g., MCI, AD, and CTE). The method may be used for the automatic staging of neurodegenerative disease for a particular patient/subject based on regional intensity and spatial patterns of the brain signals measured by PET imaging. The method may also be used to diagnose or classify the disease of a patient among multiple possibilities based on PET imaging profiles (e.g., for separating or distinguishing CTE from AD).

22 Claims, 7 Drawing Sheets

(51) Int. Cl.
*A61B 5/00* (2006.01)
*A61B 6/03* (2006.01)
*A61K 51/04* (2006.01)
*G06K 9/46* (2006.01)
*G06T 7/00* (2017.01)
*G06K 9/62* (2006.01)
*G06T 7/30* (2017.01)
*A61B 5/055* (2006.01)

(52) U.S. Cl.
CPC .......... *A61B 5/4088* (2013.01); *A61B 5/7275* (2013.01); *A61B 6/037* (2013.01); *A61B 6/501* (2013.01); *A61B 6/5217* (2013.01); *A61K 51/04* (2013.01); *G06K 9/4604* (2013.01); *G06K 9/62* (2013.01); *G06T 7/0014* (2013.01); *G06T 7/11* (2017.01); *G06T 7/30* (2017.01); *A61B 5/0035* (2013.01); *A61B 5/055* (2013.01); *G06K 2209/051* (2013.01); *G06T 2207/10088* (2013.01); *G06T 2207/10104* (2013.01); *G06T 2207/30016* (2013.01)

(58) Field of Classification Search
CPC ....... A61B 6/037; A61B 5/0042; A61B 6/501; A61B 5/055; A61B 5/0035; G06T 7/30; G06T 7/0014; G06T 7/11; G06T 2207/30016; G06T 2207/10088; G06T 2207/10104; G06K 9/62; G06K 9/4604; G06K 2209/051; A61K 51/04
See application file for complete search history.

(56) References Cited

U.S. PATENT DOCUMENTS

| | | | |
|---|---|---|---|
| 6,262,254 | B1 | 7/2001 | Barrio et al. |
| 6,274,119 | B1 | 8/2001 | Barrio et al. |
| 6,660,530 | B2 | 12/2003 | Barrio et al. |
| 7,329,401 | B2 | 2/2008 | Toyokuni et al. |
| 7,341,709 | B2 | 3/2008 | Barrio et al. |
| 8,372,380 | B2 | 2/2013 | Barrio et al. |
| 8,674,101 | B2 | 3/2014 | Satyamurthy et al. |
| 8,742,139 | B2 | 6/2014 | Satyamurthy et al. |
| 8,845,999 | B2 | 9/2014 | Wright et al. |
| 8,951,480 | B2 | 2/2015 | Satyamurthy et al. |
| 9,211,520 | B2 | 12/2015 | Satyamurthy et al. |
| 9,481,705 | B2 | 11/2016 | Satyamurthy et al. |
| 9,901,413 | B2 * | 2/2018 | Hartlep .................. A61B 90/36 |
| 2004/0152068 | A1 * | 8/2004 | Goldstein ............. A61B 5/0059 435/4 |
| 2005/0273007 | A1 | 12/2005 | Burbar |
| 2007/0053831 | A1 | 3/2007 | Barrio et al. |
| 2007/0218002 | A1 * | 9/2007 | Barrio ................ A61K 51/0421 424/9.1 |
| 2008/0279846 | A1 | 11/2008 | Shi et al. |
| 2009/0220429 | A1 * | 9/2009 | Johnsen ............... A61B 5/0484 424/9.3 |
| 2009/0292478 | A1 | 11/2009 | Avinash et al. |
| 2010/0080432 | A1 * | 4/2010 | Lilja ..................... G06T 7/0012 382/131 |
| 2010/0152577 | A1 * | 6/2010 | Young .................. A61B 6/5247 600/431 |
| 2010/0298389 | A1 | 11/2010 | Elmaleh et al. |
| 2011/0160543 | A1 * | 6/2011 | Parsey ................... A61B 5/055 600/300 |
| 2013/0066392 | A1 * | 3/2013 | Simon ..................... A61N 1/40 607/45 |
| 2013/0131490 | A1 * | 5/2013 | Huston, III ............ A61B 5/055 600/410 |
| 2014/0018649 | A1 * | 1/2014 | Jespersen ............. A61B 3/1233 600/322 |
| 2014/0226882 | A1 * | 8/2014 | Collins .................. A61B 5/055 382/128 |
| 2014/0255301 | A1 * | 9/2014 | Chen .................... C12Q 1/6883 424/1.49 |
| 2015/0080703 | A1 * | 3/2015 | Reiman ................ A61B 5/4848 600/409 |
| 2015/0182118 | A1 * | 7/2015 | Bradbury ............... A61B 1/043 600/431 |
| 2016/0203599 | A1 * | 7/2016 | Gillies ................... A61B 6/463 382/132 |
| 2016/0245828 | A1 * | 8/2016 | Roberts ................ A61B 5/4076 |
| 2018/0204327 | A1 * | 7/2018 | Matthews ............. G06K 9/623 |

OTHER PUBLICATIONS

Protas, Hillary D. et al., Prediction of cognitive decline based on hemispheric cortical surface maps of FDDNP PET, NeuroImage 61 (2012) 749-760.

Braak, H. et al., Neuropathological stageing of Alzheimer-related changes, Acta Neuropathol (1991) 82: 239-259.

Folstein, Marshal F. et al., "Mini-Mental State" A Practical Method for Grading the Cognitive State of Patients for the Clinician, J. psychiat. Res., 1975, vol. 12, pp. 189-198. Pergamon Press, Printed in Great Britain.

Logan, Jean et al., Distribution Volume Ratios Without Blood Sampling from Graphical Analysis of PET Data, J Cereb Blood Flow Metab, vol. 16, No. 5, 1996, 834-840.

Wong, Koon-Pong et al., Estimation of Input Function and Kinetic Parameters Using Simulated Annealing: Application in a Flow Model, IEEE Transactions on Nuclear Science, vol. 49, No. 3, Jun. 2002, 707-713.

Heap, B.R., Permutations by interchanges, undated, (2pages).

Barrio, Jorge R. et al., In vivo characterization of chronic traumatic encephalopathy using [F-18]FDDNP PET brain imaging, PNAS, Published online Apr. 6, 2015, E2039-E2047.

Faul, Mark et al., Traumatic Brain Injury in the United States, Emergency Department Visits, Hospitalizations and Deaths 2002-2006, U.S. Department of Health and Human Services Centers for Disease Control and Prevention, www.cdc.gov/TraumaticBrainInjury (74pages).

Grossberg, George T. et al., The Art of Sharing the Diagnosis and Management of Alzheimer's Disease with Patients and Caregivers: Recommendations of an Expert Consensus Panel, Prim Care Companion J Clin Psychiatry; 2010; 12(1); PCC.09cs00833.

Beard, John R. et al., The World report on ageing and health: a policy framework for healthy ageing, www.thelancet.com, vol. 387, May 21, 2016, 2145-2154.

Langlois, Jean A. et al., The Epidemiology and Impact of Traumatic Brain Injury, J Head Trauma Rehabil, vol. 21, No. 5, pp. 375-378 (2006).

Liu, Jie et al., High-Yield, Automated Radiosynthesis of 2-(1-Δ6-[(2-[18F]Fluoroethyl)(methyl)amino]-2-napthyl}ethylidene)malononitrile([18F]FDDNP) Ready for Animal or Human Administration, Mol Imaging Biol (2007) 9:6-16. DOI: 10.1007/s11307-006-0061-4.

Okie, Suan, Traumatic Brain Injury in the War Zone, N Engl J Med 352;20, www.nejm.org, May 19, 2005, 2043-2047.

Tauber, Clovis et al., Brain [18F]FDDNP Binding and Glucose Metabolism in Advanced Elderly Healthy Subjects and Alzheimer's Disease Patients, Journal of Alzheimer's Disease, 36 (2013) 311-320.

Thompson, Paul M. et al., Detection and Mapping of Abnormal Brain Structure with a Probabilistic Atlas of Cortical Surfaces, Journal of Computer Assisted Tomography, vol. 21(4), Jul./Aug. 1997, pp. 567-581.

Wong, K. et al., A novel data-driven approach to order subjects with neurodegenerative disease based on PET imaging data alone, Supplement to the Journal of Nuclear Medicine, The Official Publication of SNMMI, SNMMI 2015 Annual Meeting Scientific Abstracts Search 2015 Annual Meeting abstracts online starting May 15, 2015 (http://jnm.snmjournals.org), JNM, vol. 56, Supplement 3, May 2015.

(56) References Cited

OTHER PUBLICATIONS

Wong, Koon-Pong et al., A semi-automated workflow solution for multimodal neuroimaging: application to patients with traumatic brain injury, Brain Informatics (2016) 3:1-15. DOI 10.1007/s40708-015-0026-y.

Croes, G. A., A Method for Solving Traveling-Salesman Problems, Operations Research, Nov.-Dec. 1958, 791-812.

Della Croce, Federico, Generalized pairwise interchanges and machine scheduling, European Journal of Operational Research, 83 (1995) 310-319.

Wong, Koon-Pong et al., Simplified quantification of FDDNP PET studies, J Nucl Med, May 2011, vol. 52, No. supplement 1, 104.

Durstenfeld, Richard, Algorithms, Communications of the ACM, vol. 7, No. 7, Jul. 1964.

Wong, Koon-Pong, A Novel Data-Driven Approach to Order Subjects with Neurodegenrative Disease Based on PET Imaging Data Alone, UCLA, Departments of Molecular and Mediacal Pharmacology, Psychiatry and Biobehavioral Sciences, and Biomathematics, David Geffen School of Medicine at UCLA, Los Angeles, California, undated, undated, (1page).

PCT International Search Report for PCT/US2017/057260, Applicant: The Regents of the University of California, Form PCT/ISA/210 and 220, dated Mar. 1, 2018 (5pages).

PCT Written Opinion of the International Search Authority for PCT/US2017/057260, Applicant: The Regents of the University of California, Form PCT/ISA/237, dated Mar. 1, 2018 (6pages).

Rissanen, Eero et al., Automated reference region extraction and population-based input function for brain [11C] TMSX PET image analyses, Journal of Cerebral Blood Blow & Metabolism (2015) 35, 157-165.

PCT Invitation to Pay Additional Fees for PCT/US2017/057260, Applicant: The Regents of the University of California, Form PCT/ISA/237, dated Jan. 9, 2018 (3pages).

* cited by examiner

METHOD FOR POSITRON EMISSION TOMOGRAPHY (PET) IMAGING ANALYSIS FOR CLASSIFYING AND DIAGNOSING OF NEUROLOGICAL DISEASES

RELATED APPLICATION

This Application claims priority to U.S. Provisional Patent Application No. 62/409,724 filed on Oct. 18, 2016, which is hereby incorporated by reference in its entirety. Priority is claimed pursuant to 35 U.S.C. § 119 and any other applicable statute.

TECHNICAL FIELD

The technical field generally relates to automated methods of analyzing positron emission tomography (PET) images for unbiased imaging analysis in clinical settings. More specifically, the technical field relates to automated image analysis methods for classifying and staging of neurological diseases.

BACKGROUND 2-(1-{6-[(2-[F-18]fluoroethyl)(methyl)amino]-2-naphthyl}ethylidene)-malononitrile ([F-18]FDDNP) PET imaging has been used for classifying and staging progressive diseases, including Alzheimer's disease (AD) and Chronic Traumatic Encephalopathy (CTE). More than a decade of clinical research experience in the U.S., Europe, and Asia has demonstrated the ability of [F-18]FDDNP to differentiate Alzheimer's disease (AD) from normal aging, mild cognitive impairment (MCI), and several other neurodegenerative diseases (e.g., progressive supranuclear palsy, dementia with Lewy bodies, and Down syndrome). The ability of [F-18]FDDNP to differentiate AD from normal aging is comparable to that of 2-deoxy-2[F-18]fluoro-D-glucose ([F-18]FDG).

Moreover recent clinical research demonstrates a distinct [F-18]FDDNP binding pattern in retired athletes and military personnel with a history of traumatic brain injury and suspected CTE; and this pattern can be readily differentiated from that of AD. Currently there is no available biomarker that can detect suspected CTE in living people at risk, and other PET ligands for this purpose are very early in their development.

The clinical symptoms of suspected CTE and AD overlap making accurate diagnosis challenging particularly in older individuals when the risk of AD increases. Both suspected CTE and AD patients experience cognitive decline and dementia as well as behavioral and mood symptoms. Having an accurate tool that assists in the differentiation of these common late life conditions would be important. Moreover, in younger adults, identifying patients with suspected CTE from normal individuals would be important for assisting with enrollment in clinical trials of drug discovery or treatment.

The diagnosis of CTE is currently only confirmed at autopsy, and there is a tremendous need for a biomarker that can identify suspected CTE in living individuals. Such a biomarker would guide current treatment decisions: differentiating AD from suspected CTE would identify those patients with AD who would be most likely to respond to medications currently available for that condition. Although no effective treatments are yet available, preventive measures can be implemented if suspected CTE is identified, and, moreover, these individuals could be enrolled in appropriate clinical trials.

While [F-18]FDDNP PET imaging has been used for classifying and staging progressive diseases such as AD and CTE, accurate reading and interpretation of these images require experts who are nuclear medicine physicians or neurologists experienced in brain PET imaging to perform the task. Without established reading procedures, the interpretation of [F-18]FDDNP PET imaging results can be subjective.

Progressive neurological diseases involve gradual changes in disease-specific brain structures. If the number of brain structures involved is small (e.g., one or two structures), the changes tagged by a PET tracer (like [F-18] FDDNP or [F-18]FDG) and imaged with PET can be viewed by experts to determine the type of disease and the progressive stage, especially for large and monotonous changes. However, when there are multiple structural regions involved and the changes are subtle, it is frequently difficult for most practitioners to read the images to differentiate AD and CTE.

SUMMARY

For progressive neurodegenerative diseases such as AD and CTE, functional and structural changes in specific brain regions occur gradually and these changes become more prominent with increased disease severity. As described herein, the [F-18]FDDNP PET imaging method addresses: (1) the determination of the progressive course of regional brain PET activities for a progressive disease, (e.g., CTE, MCI, and AD); (2) the staging of the disease for a particular patient/subject based on regional intensity and spatial patterns of the brain signals measured by PET imaging, and (3) the diagnosing or identification of the disease of the patient/subject among multiple possibilities based on PET imaging profiles (e.g., for separating or distinguishing CTE from AD).

In one aspect, the method involves providing a computer accessible database containing region of interest (ROI) images or ROI values of a population of subjects with the neurodegenerative disease at different stages obtained with in vivo PET images using a radiotracer such as [F-18] FDDNP, wherein the different regions of interest (ROIs) of the population of subjects are used to order the population of subjects by minimizing a total distance measure as represented by the formula: $\Sigma_{i=1}^{m-1}\Sigma_{j=1}^{n}|ROI_{i,j}-ROI_{i+1,j}|$, where $ROI_{i,j}$ is the image value at structural region j of an $i^{th}$ subject, n is the number of structural regions, and m is the number of total subjects.

A magnetic resonance image (MRI) of the patient's/subject's brain as well as in vivo PET images of the subject's brain are obtained using the radioactive tracer. In some embodiments, these are dynamic PET images. In other embodiments, the images may include static PET images. The PET images are elastically mapped to a common space using the magnetic resonance image as a guide. For dynamic PET scans, distribution volume ratio (DVR) images of the subject's brain are generated and mapped onto the common space, wherein an ROI atlas for a plurality of different brain regions was pre-defined, each region being a different ROI. DVR values are extracted for each different ROI for the subject. The extracted DVR values of a set of ROIs are compared to the DVR values of the corresponding ROIs in the database of the population of subjects with a known disease and/or disease stage; and the stage of the neurodegenerative disease for the patient/subject is characterized on this comparison. This comparison may involve identifying an ordering location for the subject within the population of subjects using the extracted DVR values (e.g., mathematically calculating a location in the data set that yields the least total distance from the existing data set). For static PET images, instead of DVR images, standardized uptake value ratio (SUVR) images are used and SUVR values are extracted.

In one embodiment, a method of characterizing a neurodegenerative disease in a subject using positron emission tomography (PET) includes the operations of obtaining a magnetic resonance image of the subject's brain (with a MRI scanning device). In vivo PET images of the subject's brain are obtained (using a PET scanning device) after a radioactive tracer is administered to the subject. The PET images are mapped to a common space using the magnetic resonance image. Distribution volume ratio (DVR) images of the subject's brain are generated and mapped onto the common space, wherein the DVR images comprise a plurality of different brain regions, each region defining a different region of interest (ROI). DVR values are then extracted for the ROIs of the subject. A computer accessible database is provided that contains DVR values for the population of subjects with the neurodegenerative disease at different stages obtained with in vivo PET images using the radiotracer. Next, using the DVR values of the different regions of interest (ROIs) of the subject, the subject is ordered among the population of subjects by minimizing a total distance measure as represented by: $\Sigma_{i=1}^{m-1}\Sigma_{j=1}^{n} |ROI_{i,j}-ROI_{i+1,j}|$, where $ROI_{i,j}$ is the DVR value at structural region j of an $i^{th}$ subject, n is the number of structural regions, and m is the number of total subjects. This process is carried out by software that is executed by the computer or other computing device. The neurodegenerative disease for the subject is then characterized based on the ordering of the subject in the population of subjects.

In another embodiment, a method of characterizing neurodegenerative disease in a subject using positron emission tomography (PET) includes providing a computer accessible database containing region of interest (ROI) images or ROI values of a population of subjects with the neurodegenerative disease at different stages obtained with in vivo PET images using a radiotracer. The ROI values may include, for example, DVR values or perfusion values for a particular ROI. A magnetic resonance image of the subject's brain is obtained along with in vivo PET images of the subject's brain after the radioactive tracer is administered to the subject. The PET images are then mapped to a common space using the magnetic resonance image. Distribution volume ratio (DVR) images of the subject's brain are generated and mapped onto the common space, wherein the DVR images comprise a plurality of different brain regions, each region defining a different ROI. DVR values are extracted for each different ROI for the subject (in some embodiments perfusion values may also be extracted). A software algorithm is executed on a computer that uses the DVR values of each different ROI (and in some embodiments also perfusion values) to order the subject among the population of subjects by minimizing a total distance measure as represented by: $\Sigma_{i=1}^{m-1}\Sigma_{j=1}^{n}|ROI_{i,j}-ROI_{i+1,j}|$, where $ROI_{i,j}$ is the image value at structural region j of an $i^{th}$ subject, n is the number of structural regions, and m is the number of total subjects. The stage or severity of the neurodegenerative disease is characterized for the subject based on the ordering.

In another embodiment, a method of diagnosing neurodegenerative disease in a subject using positron emission tomography (PET) includes providing a computer accessible database containing brain region specific distribution volume ratio (DVR) values and/or perfusion values of a first population of subjects with Alzheimer's disease (AD) and a second population of subjects with Chronic Traumatic Encephalopathy (CTE) obtained using a radiotracer, wherein the first population of subjects and the second population of subjects are ordered according to their disease state progression. A magnetic resonance image of the subject's brain is obtained. In vivo dynamic PET images of the subject's brain are obtained after the radioactive tracer is administered to the subject. Distribution volume ratio (DVR) images are generated and registered with the magnetic resonance image of the subject's brain and mapped onto the common space. Brain region specific DVR values and/or perfusion values of the subject are extracted from the PET images. The brain region specific extracted DVR values and/or perfusion values of the subject are compared to the brain region specific DVR values and/or perfusion values stored in the database of the first population of subjects and the second population of subjects, wherein the comparison involves software computing a distance between the DVR values and/or perfusion values of the subject and the DVR and/or perfusion values of the first population and the second population. The neurodegenerative disease is diagnosed as either AD or CTE for the subject based on the computed distance. For example, if the subject's data has the closest distance to CTE subjects, the subject will be diagnosed with CTE.

In another embodiment, a method of characterizing neurodegenerative disease in a subject using positron emission tomography (PET) includes providing a computer accessible database containing region of interest (ROI) images or ROI values of a population of subjects with the neurodegenerative disease at different stages obtained with in vivo static PET images using a radiotracer. A magnetic resonance image of the subject's brain is obtained along with in vivo static PET images of the subject's brain obtained after the radioactive tracer is administered to the subject. The PET images are mapped to a common space using the magnetic resonance image. Standardized uptake value ratio (SUVR) images of the subject's brain are generated and mapped onto the common space, wherein the SUVR images comprise a plurality of different brain regions, each region defining a different ROI. SUVR values for each different ROI for the subject are extracted. A software algorithm is executed on a computer that uses the SUVR values of each different ROI to order the subject among the population of subjects by minimizing a total distance measure as represented by: $\Sigma_{i=1}^{m-1}\Sigma_{j=1}^{n}|ROI_{i,j}-ROI_{i+1,j}|$, where $ROI_{i,j}$ is the image value at structural region j of an $i^{th}$ subject, n is the number of structural regions, and m is the number of total subjects. The stage or severity of the neurodegenerative disease for the subject is then characterized based on the ordering.

DETAILED DESCRIPTION OF ILLUSTRATED EMBODIMENTS

Figure 1:
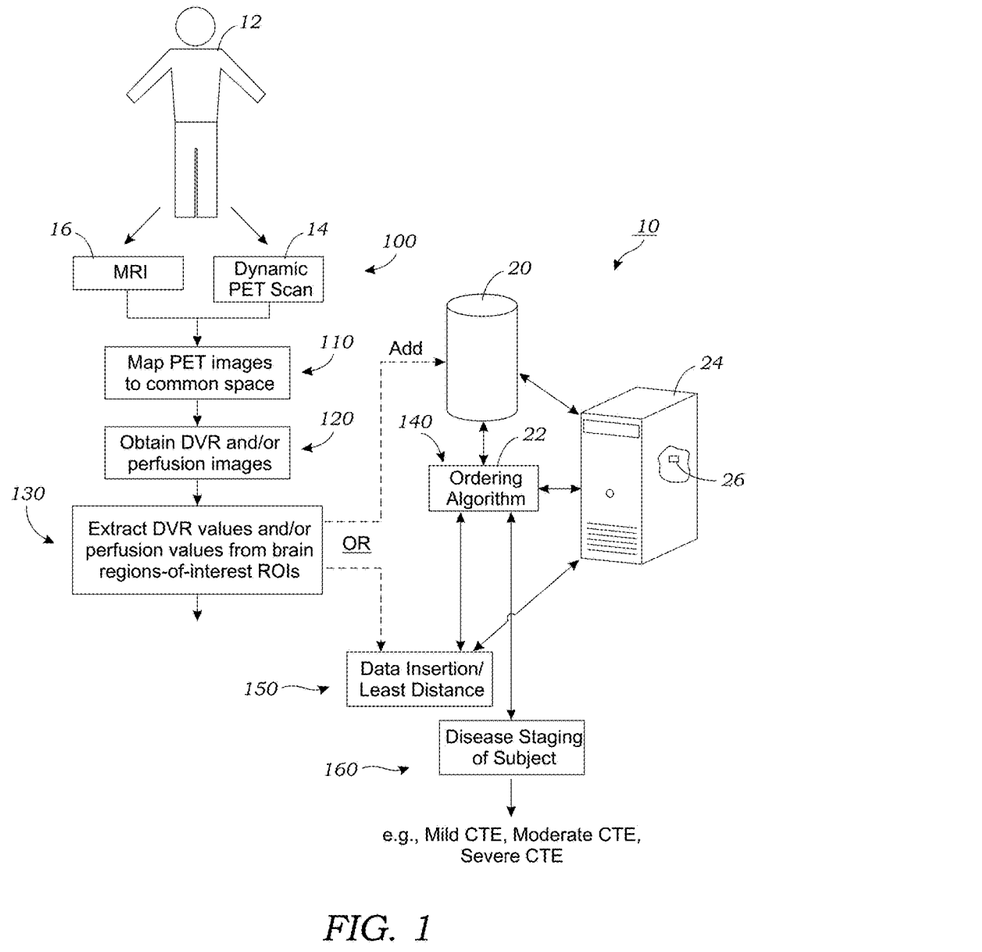
FIG. 1 illustrates a system and method that is used to characterize the progression or staging of neurodegenerative disease in a subject or patient.

FIG. 1 illustrates a system 10 and method that is used to characterize the progression or staging of a neurodegenerative disease in a subject or patient 12. The neurodegenerative disease may include AD, CTE, as well as Mild Cognitive Impairment (MCI). The system uses in vivo dynamically obtained PET images of a subject acquired using a dynamic PET scanner 14. A subject is given a radiotracer such as [F-18]F-FDDNP for the dynamic PET scan although it is not limited to a specific radiotracer. Magnetic Resonance Imaging (MRI) 16 is also used with the subject or patient 12. Operation 100 illustrates obtaining PET scan images as well as MRI images of the subject or patient 12. It should be appreciated that the PET scan images and MRI images may be obtained using a separate PET scanner 14 and MRI scanner 16. Alternatively, the PET scan images and the MRI images may be obtained by a single scanner that has both PET and MRI imaging functionality (e.g., combined MRI-PET scanner).

The MRI images are obtained so that PET images obtained from PET scanner 14 can be registered with and mapped to a common space as illustrated in operation 110. In order to extract PET images (and values therefrom) from different patients and subjects automatically and reliably, the PET image of the subject/patient is normalized spatially to a standard reference template defined on a common space. For example, PET Distribution Volume Ratio (DVR) images may be mapped to a MRI derived hemispheric cortical surface map that is warped into a common space. Such a technique is disclosed in Protas et al., Prediction of cognitive decline based on hemispheric cortical surface maps of FDDNP PET, NeuroImage, 61, pp. 749-760 (2012), which is incorporated by reference herein. Another method of normalization is MRI-based elastic mapping which permits the automated regional brain signal quantification from PET images. For example, K. P. Wong et al. describe a workflow solution that combines the use of non-linear spatial normalization of structural brain images and template-based anatomical labeling to automate the region-of-interest (ROI) analysis. See K. P. Wong et al., A semi-automated workflow solution for multimodal neuroimaging: application to patients with traumatic brain injury, Brain Informatics, 3, pp. 1-15 (2016), which is incorporated by reference herein. Other mapping schemes may also be used with the invention described herein including, for example, using a probabilistic atlas of the human brain on high-dimensional fluid transformations such as that disclosed in Thompson et al., Detection and Mapping of Abnormal Brain Structure with a Probabilistic Atlas of Cortical Surfaces, J. of Computer Assisted Tomography, Vol. 21(4), pp. 567-581 (1997), which is incorporated by reference herein. The mapping process may also use early-summed (e.g., 0 to 6 minute post-injection of the radiotracer) PET perfusion images as part of the normalization process to obtained PET images.

Figure 4:
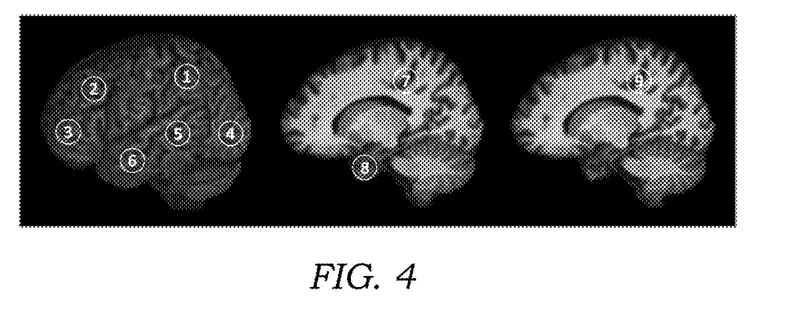
FIG. 4 illustrates various cortical surface regions of interest (ROIs) in a human brain (DVR values of parietal #1, frontal #2, prefrontal #3, occipital #4, parietal-temporal border #5, lateral temporal #6, posterior cingulate #7, and medial temporal #8, plus the perfusion value at the posterior cingulate #9) that have been used for staging the progression of AD subjects.

The now mapped PET images are converted to parametric images of distribution volume ratio (DVR or DVR images) as illustrated in operation 120. The DVR is a function of receptor availability and is widely used in brain PET imaging studies. In some instances, the perfusion images are obtained instead of, or in addition to, DVR images as illustrated in operation 120 of FIG. 1. Next, with reference to operation 130 in FIG. 1, the DVR images (or perfusion images) are used to extract a DVR value (or perfusion value) for a specific spatial region of the brain. In one embodiment of the invention, multiple spatial regions or regions of interest (ROIs) of the brain are used to characterize, identify, and/or diagnose neurodegenerative disease in a subject or patient 12. DVR values are commonly used to model receptor availability and correlate the receptor availability of a particular ROI to a normalized region such as the cerebellum. For example, DVR values or ratios may generally range from about 0.8 to about 2.0 (DVR values may still fall outside of this range and still be capture by the inventive methods described herein) for one of the anatomical ROIs used in connection with system 10 and method described herein. Perfusion values or ratios measure the degree of perfusion in a particular ROI of the subject's brain as compared a reference region (e.g., entire or whole brain). For example, perfusion values or ratios that are obtained for the PET scanner 14 may range from about 1.2 to 2.0, although it should be understood that the invention is not limited to this particular range. Depending on the particular neurodegenerative disease different ROIs may be used. FIG. 4, for example, illustrates eight (8) cortical ROIs that are used in one aspect of the invention for staging and diagnosis of AD. These include parietal #1, frontal #2, prefrontal #3, occipital #4, parietal-temporal border #5, lateral temporal #6, posterior cingulate #7, and medial temporal #8. DVR values are extracted for each of these regions. Note that one region, the posterior cingulate #9, was used for both DVR images and early perfusion images. Extracted perfusion values in combination with extracted DVR values may be used for ordering or staging of subjects 12 as described herein.

Referring back to FIG. 1 and as explained herein, the DVR values (and/or perfusion values) extracted from the various ROIs in the subject 12 are used in part of an automated process that characterize, identify, and diagnose neurodegenerative disease in the subject or patient 12. In addition to DVR values, perfusion values obtained from perfusion images (e.g., early-summed (e.g., 0-6 min.) perfusion images in the PET scan process) can be used to extract perfusion values for a particular ROI that is also used in part of an automated process that characterize, identify, and diagnose neurodegenerative disease in a subject or patient. Typically, the extracted DVR or perfusion values for a particular ROI represent an average or mean value for the specific ROI. That is to say, the extracted DVR or perfusion value is not obtained from a single voxel but is instead averaged over a larger area defined by the spatial area of the particular ROI.

As seen in FIG. 1, in one embodiment, the system 10 includes a computer accessible database 20 or storage repository that contains DVR values and/or perfusion values that have been obtained from PET images of a population of subjects having a known neurodegenerative disease and given the same radiotracer. Data that is stored in the database 20 may include the raw PET images themselves and/or extracted DVR values and/or perfusion values from the ROIs of the subjects 12. These values that are stored in the database 20 may also be associated with one or more qualitative or quantitative assessments as to the progression or severity of the particular subject's 12 neurodegenerative disease (e.g., mild, moderate, severe). Clinical and behavioral assessments, like Mini-Mental State Examination (MMSE) score for dementia symptoms for the subjects or patients, are typical of this kind of information and could also be stored in the database 20. See Folstein M F et al., Mini-mental state: A practical method for grading the cognitive state of patients for the clinician, J Psychiatr Res. 12:189-198, 1975, which is incorporated by reference herein. The database 20 may include a "local" database that is maintained at a local healthcare facility (e.g., maintained by a single hospital). Alternatively, the database 20 may be a "remote" database 20 that can be populated with data from subjects 12 located at different medical facilities across different geographic regions. The database 20 may be an open-access database or the database may be a proprietary database that is accessible only to selected users or institutions.

In addition, the database entries for these subjects 12 may also include the identification of the neurodegenerative disease (e.g., MCI, AD, or CTE). As explained herein, the database 20 may also store patient ordering or ranking information of all or some of the patient data contained in the database 20. This ordering or ranking may be dynamically updated, for example, as data from new subjects 12 is added to the database 20. As disclosed herein, subjects 12 or patients may be automatically ordered in terms of disease severity and/or disease progression using a software-based ordering algorithm that uses DVR and/or perfusion values extracted from the various ROIs of the DVR and perfusion. The patient ordering or ranking may include the most recent or updated ranking of subjects within the database 20.

In one particular aspect of the invention, the subjects 12 that have data stored in the database 20 are subject to an automated ordering or permutation process 140 that orders these subjects 12 in terms of the subject's disease severity/progression. In one aspect, from a cohort of patients 12 with the same neurological disease of various progression stages, the right ordering of these patients 12 in terms of their disease severity/progression is the ordering that has the smallest inter-subject distance of image values (e.g., DVR and/or perfusion values) in their disease-specific brain regions between adjacent subjects in the ordering (i.e., the smoothest when plotted against the ordering). In mathematical terms, the right ordering should have the minimal value or "cost function" for the following total distance measure as shown in Eq. 1 below.

$$\text{Total distance} = \Sigma_{i=1}^{m-1} \Sigma_{j=1}^{n} |ROI_{i,j} - ROI_{i+1,j}| \quad \text{Eq. 1}$$

Where $ROI_{i,j}$ is the image value (e.g., extracted DVR value or extracted perfusion value) at structural region j (=1,...,n) of the $i^{th}$ patient in a particular ordering, n is the number of structural regions, and m is the total number of subjects. The set of n structural regions is disease-specific. For AD or MCI this includes (with reference to FIG. 3) parietal #1, frontal #2, prefrontal #3, occipital #4, parietal-temporal border #5, lateral temporal #6, posterior cingulate #7, and medial temporal #8. For CTE, this includes frontal, anterior cingulate, amygdala, hypothalamus, and midbrain. In Eq. 1, if the summation over subjects is removed, the value obtained is referred to as the distance between two adjacent subjects i and i+1. The goal of the ordering process or algorithm is to find an ordering or permutation of the m subjects that minimizes the total distance. With reference to FIG. 1, the ordering or permutation is carried out using software 22 that executes the ordering algorithm on the patient/subject data contained in the database 20. The software 22 is executed using one or more computers 24 that contain one or more processors 26 therein. The computer 24 may include, for example, a personal computer, server, or multiple computers linked together for parallel processing to improve processing speed. The computer 24 may be a local computer that is located with or near the PET scan 14 and/or the MRI 16. The computer 24 may also be a remotely located computer that is not physically located near the PET scan 14 and/or the MRI 16. For example, the computer 24 may include a remotely located computer such as a physical or virtual server, cluster of physical or virtual servers, or cloud-based computing device or devices. In such a case, data and/or images may be communicated across a wide area network. The computer 24 may also include the computer that is used for image acquisition/data analysis for the PET scan 14 and/or the MRI 16.

The ordering or permutation may be accomplished by using a conventional fast permutation generation method which generates all possible permutations and then selects the best ordering that produces the smallest total distance using Eq. 1. An example of this method is disclosed in Heap B R, Permutations by interchanges, Comput J. 6:293-294, 1963, which is incorporated by reference herein. This method may be appropriate when the number of subjects (m) is small. Another option is to use a pairwise interchange (swapping) heuristic to swap two randomly selected subjects in a current ordering. See Della Croce F, Generalized pairwise interchanges and machine scheduling, European Journal of Operational Research, 83:310-319, 1995, which is incorporated by reference herein. The initial ordering of the cohort of subjects can be generated using the Fisher-Yates shuffle method as described in Durstenfeld R, Algorithm 235: Random permutation. Communications of the ACM. 7(7):420 (1964), which is also incorporated by reference herein.

In an alternative method, a simple local search (2-Opt) heuristic is performed in-place, with iterative reversal of the ordering defined by two randomly selected subjects p and q inclusively such that the total distance is reduced upon reversing the order, when optimizing the total distance for all subjects using a simulated annealing algorithm. Croes et al., which is incorporated herein by reference, describes an example of such a 2-Opt heuristic that can be employed to optimize the total distance. See Croes G A, A method for solving traveling-salesman problems, Operations Research, 6(6):791-812, 1958. The initial ordering of the cohort of subjects can be generated using the Fisher-Yates shuffle method as described in Durstenfeld R., supra. The simulated annealing algorithm is a preferred approach because of its ability to find global minimum and avoid becoming trapped in local minimums. An example of a simulated annealing algorithm may be found in Wong K-P et al., Estimation of input function and kinetic parameters using simulated annealing: Application in a flow model, IEEE Trans Nucl Sci. 49(3):707-713, 2002, which is incorporated herein by reference.

In one embodiment, during the ordering optimization process for determination of the best ordering for all subjects 12, the total distance and the ordering are not re-computed for all subjects 12 and regions at every iteration. Instead, the total distance and the ordering are updated only when a change in the total distance occurs (e.g., when subjects being swapped at two positions in the ordering or a reversal of a local ordering) and the computation is performed only at the locations where changes take place so as to minimize the computational time and memory requirements by the optimization algorithm. Once the ordering is determined, the course of progressive changes of the image value at region j becomes known. Of course, it is possible to use a "brute force" approach to re-compute the total distance for all subjects 12 and ROIs at every iteration (as each subject is added) although this significantly increases the computation resources that are required. Regardless, the ordering algorithm that is implemented using software 22 is executed by one or more processors 26 contained in a computer 24 as is illustrated in FIG. 1.

In one embodiment of the invention, the extracted DVR and/or extracted perfusion data that is obtained from the dynamic PET scan is then incorporated or added into the database (i.e., the "Add" dashed path in FIG. 1) described above and the least distance optimization process using Eq. 1 is performed again to incorporate the subject's 12 data to obtain the least total distance. The ranking of now-incorporated subject 12 in this new or updated ordering would determine the disease stage (e.g., disease stage or progression of MCI, AD, or CTE). Alternatively, one could determine the stage by calculating the distances (e.g., Eq. 1 without summing over all subjects) of the corresponding ROI values of the new subject 12 or patient to various progression locations and finding the location that yields the least "distance." This alternative data insertion/least distance path is also illustrated in FIG. 1 in operation 150. In essence, in this alternative method, rather than re-running the ordering algorithm of Eq. 1 which may take a significant amount of computational resources and time, the subject's data may be mathematically analyzed to provide the shortest distance with respect to the already ordered data. Here, instead of calculating the total distance for all subjects 12 and regions at every iteration during the optimization process, the calculation is only performed at the locations in the existing ordering where the new subject is to be placed. The total distance is then updated and compared with the "least" total distance found so far until all the locations in the ordering have been tested and the resulting "best" ordering with the new subject added is saved. This may be accomplished using software 22 executed by one or more processors 26 of the computer 24 as indicated in FIG. 1.

Figure 9:
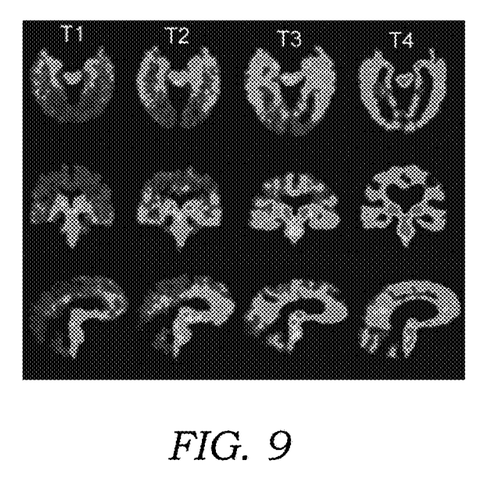
FIG. 9 shows the typical [F-18]FDDNP DVR images at four (4) stages (T1 (early), T2, T3, T4 (advanced)) of CTE.

As seen in FIG. 1, by either adding the subject's regional PET data to the database 20 and re-ordering the population or by calculating the distance of the data (e.g., DVR or perfusion data for ROIs) to the progression course of the existing ordered set using the data insertion method, the software 22 can automatically characterize the progression or staging of the neurodegenerative disease of the subject 12. For example, based on the location of the subject 12 within the ordering of cohorts, the software 22 can automatically output a qualitative or even quantitative measure of the progression or staging of the disease as illustrated in operation 160. For example, as one particular example, this may include, for example, a qualitative determination such as "mild CTE," "moderate CTE," or "severe CTE." Similar qualitative determinations may be output for MCI and AD. While three (3) qualitative bins or categories is described above, it should be appreciated that further bins or gradations for the stages may also be used. For example, as seen in FIG. 9, CTE is divided into four (4) stages: T1 (early), T2, T3, and T4 (advanced). The various cutoffs for these stages may include thresholds or statistical measures of the compared data, e.g., relative DVR or perfusion values based on the ordering of cohorts, including the relative distances between other cohorts having established qualitative determinations. For example, the distance of DVR or perfusion values to one or more patients having a similar qualitative staging may be used to assign the determination for the particular subject 12. For example, the distance of DVR and/or perfusion values for a subject 12 relative to the same values of known subjects in adjacent classifications can be used to place the subject 12 in a particular category. For example, a tested subject 12 may have smaller distance to a T2 patient (or multiple T2 patients) as compared to the distance to a T1 patient (or multiple T2 patients). Based on the closer distance to T2, the subject 12 may be classified as stage T2.

Figure 2A:
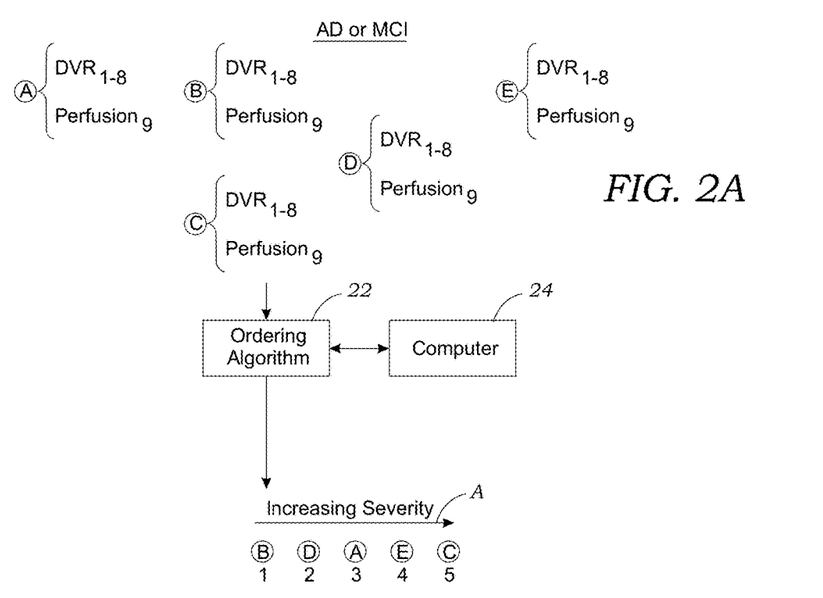
FIG. 2A schematically illustrates how the system and method are used to automatically characterize the progression or staging of a neurodegenerative disease (AD or MCI) in a plurality of subjects.

FIG. 2A schematically illustrates how the system 10 and method are used to automatically characterize the severity of a neurodegenerative disease in a plurality of subjects 12. In this example, there are five subjects 12 denoted A, B, C, D, and E and the neurodegenerative disease is AD. For each subject 12, DVR values are extracted for eight different ROIs (i.e., $DVR_{1-8}$). In addition, each subject 12 has extracted perfusion data (i.e., $Perfusion_9$ which may be obtained from a different or same region as used for the DVR values). As seen in FIG. 2A, the five subjects 12 are then run through the ordering algorithm executed by software 22. The software 22 then orders these five subjects 12 into a ranked order with subjects 12 to the right (in the direction of arrow A) having increasingly severe AD (the same could be done for MCI). Additional subjects 12 could be added and run through the ordering algorithm executed by the software 22 where the software could re-rank all subjects 12 or place the subject 12 in the appropriate ranking amongst the then existing set of cohorts.

Figure 2B:
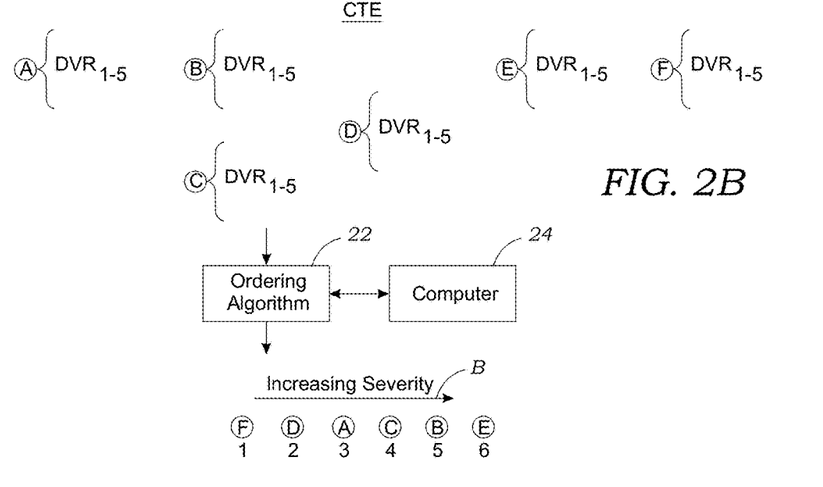
FIG. 2B schematically illustrates how the system and method are used to automatically characterize the progression or staging of a neurodegenerative disease (CTE) in a plurality of subjects.

FIG. 2B illustrates a similar schematic of how the system 10 and method are used to automatically characterize the progression or staging of a neurodegenerative disease in a plurality of subjects 12, although in this example, the subjects 12 are being ordered or ranked for the neurodegenerative disease CTE. For each subject 12, DVR values are extracted for five different ROIs (i.e., $DVR_{1-5}$). In this particular example, perfusion values are not used in the ordering algorithm although in other embodiments they could possibly be used. As seen in FIG. 2B, six subjects 12 denoted A, B, C, D, E, and F are then run through the ordering algorithm executed by software 22. The software 22 then orders these six subjects 12 into a ranked order with subjects 12 to the right (in the direction of arrow B) having increasingly severe CTE. Additional subjects 12 could be added or run through the ordering algorithm executed by the software 22 where the software could re-rank all subjects 12 or place the subject 12 in the appropriate ranking amongst the then existing set of cohorts.

Figure 3:
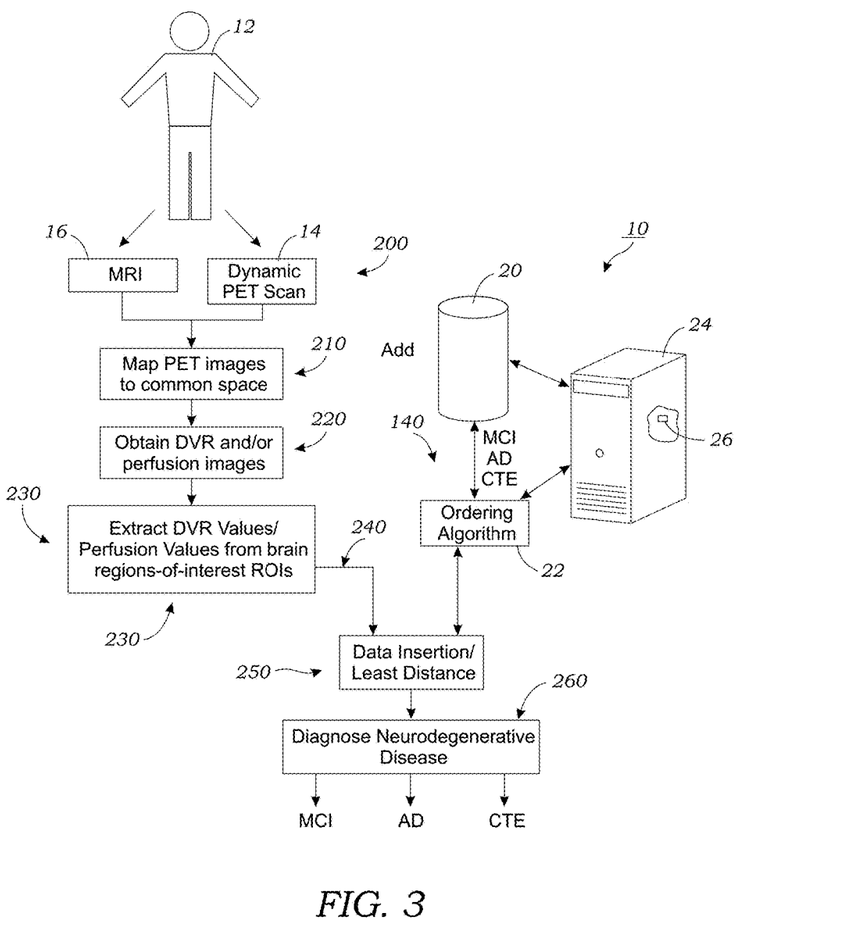
FIG. 3 illustrates a system and method that is used to identify or diagnose neurodegenerative disease in a subject or patient.

In another aspect of the invention, as seen in FIG. 3, the subject 12 may be suffering from a neurodegenerative disease that has yet to be differentially diagnosed. For example, the invention may be able to differentiate between alternative diseases such as MCI, AD, and CTE. In this particular example, known subjects with MCI, AD, or CTE have their PET scan data (e.g., extracted DVR values, extracted perfusion values) stored in the database 20. For differential diagnosis among different alternative diseases (e.g., separating CTE from AD or MCI), one could find the "distance" of a particular patient or subject 12 using the extracted regional DVR values (or regional perfusion values) to the courses of different diseases (i.e., CTE, AD, and MCI). The computer 24 can execute software 22 to compare and evaluate these "distances" statistically to determine the type of disease that matches closest to that of the patient/subject 12, and thus also the progressive stage. For a different progressive neurological disease (e.g., CTE), one could repeat the procedure above as illustrated in FIG. 1 to determine the courses of progressive changes of the brain regions for that disease.

With reference to FIG. 3, operation 200 illustrates obtaining PET scan images as well as MRI images of the subject 12 or patient using the PET scanner 14 and MRI scanner 16. In this embodiment, it is unclear whether the subject 12 or patient has MCI, AD, or CTE. The MRI images are obtained so that PET images obtained from PET scanner 14 can be registered with and mapped to a common space as illustrated in operation 210. The now mapped PET images are converted to parametric images of distribution volume ratio (DVR or DVR images) as illustrated in operation 220. Next, with reference to operation 230 in FIG. 3, the DVR and/or perfusion images are used to extract a DVR value and/or perfusion value for specific spatial regions (i.e., ROIs) of the brain. As seen in operation 240, the patient data (i.e., DVR and/or perfusion values for a plurality of ROIs) are then input to the ordering software 22. In this particular example, the data insertion method is used as seen in operation 250. The software 22 can then calculate the distances of the subject's 12 data relative to the known data stored in the database 20 for subjects with known neurological diseases such as MCI, AD, and CTE. The disease state that provides the closest or smallest distance to the subject 12 is deemed to be the most accurate disease diagnosis which can then be output or presented to the computer operator as illustrated in operation 260.

Note that the method of calculation of the "total distance" using Eq. 1 permits the addition of weighting factors for different regional (ROI) image values to account for their different quantitative significance in disease progression, their different sizes, and their different variability or noise levels. Also, for different diseases, the weighting factors could be different. Other forms of "total distance," like the square or other powers of the image activity difference between adjacent subjects in the ordering can also be used to account for different variation and outlier conditions. In fact, the "total distance" could even include terms that use information not derived from PET images or unrelated to imaging. Clinical and behavioral assessments, like MMSE score for dementia symptoms, are typical of this kind of information and could also be stored in the database.

Experimental

The above-described method to automatically determine the staging or progression of a neurodegenerative disease was used to characterize the staging of patients with AD. AD is the most common form of neurodegenerative disorder in the elderly, having two characteristic neuropathological hallmarks: β-amyloid plaque (Aβ) and neurofibrillary tangle (NFT). In vivo PET imaging using [F-18]FDDNP has been shown to provide good visualization of AD progression consistent with brain neuro-aggregate distribution determined in autopsied brain from AD patients. It was hypothesized that a cohort of subjects at different stages of the same degenerative disease sampled from a larger population can be permuted in an order representative of disease progression if the disease-specific pathologies are measurable. The model-independent approach described herein was proposed to order patients with MCI and AD using regional [F-18]FDDNP binding which measured the level of Aβ and NFT deposition. The ordering results were validated with independent measurements from neuropsychological test.

Dynamic [F-18]FDDNP PET scans and MRI scans were performed on eight (8) MCI and seven (7) AD patients. Standard neuropsychological tests, including MMSE scores, were performed on all subjects. Parametric images of distribution volume ratio (DVR) generated by Logan analysis using cerebellum as reference region and by normalizing the early-summed (0-6 min.) perfusion-like [F-18]FDDNP image by its whole-brain averaged value. Reference to Logan analysis and DVR values may be found in Logan J. et al., Distribution volume ratios without blood sampling from graphical analysis of PET data. J Cereb Blood Flow Metab. 16:834-840, 1996, which is incorporated herein by reference.

A hemispheric cortical surface map (HCSM) for each subject was extracted from the MRI in ICBM space as described in Protas et al, supra. The same transformations were applied to the DVR and summed [F-18]FDDNP perfusion images to place them in the same cortical space. FIG. 4 shows a set of cortical regions of interest (ROIs) that were drawn directly on the average HCSM and mapped to DVR and early-summed [F-18]FDDNP perfusion images to extract regional values.

For this experiment, it was assumed that: (1) the disease progresses gradually from one stage to another; and (2) subjects having the same disease of the same (or similar) stage would possess a similar spatial pattern of biomarkers (regional variables such as DVR and perfusion) which is different from those subjects at a more early or advanced stage. Thus, subjects at different stage of the same disease sampled from a larger subject population can be permuted in an order representative of disease progression by minimizing the total variations of various regional binding (DVR) and perfusion data between two adjacent subjects using the cost function of Eq. 1 described above.

The optimal order could be used to predict the staging of the disease and the ordered regional measurements would show temporal change as the disease progresses. Combinatorial computation was implemented in-house using C programming language (compiled and built by Visual Studio 2010) on a DELL desktop computer (OptiPlex 9010, CPU: Core i7-3770 3.4 GHz; RAM: 8 GB) running Microsoft Windows 7. Independent measurements obtained from standard MMSE tests were used to validate the ordering obtained by the proposed new method. The performance of the new method was also compared to the inverse prediction method described in Protas et al., supra.

Figure 5:
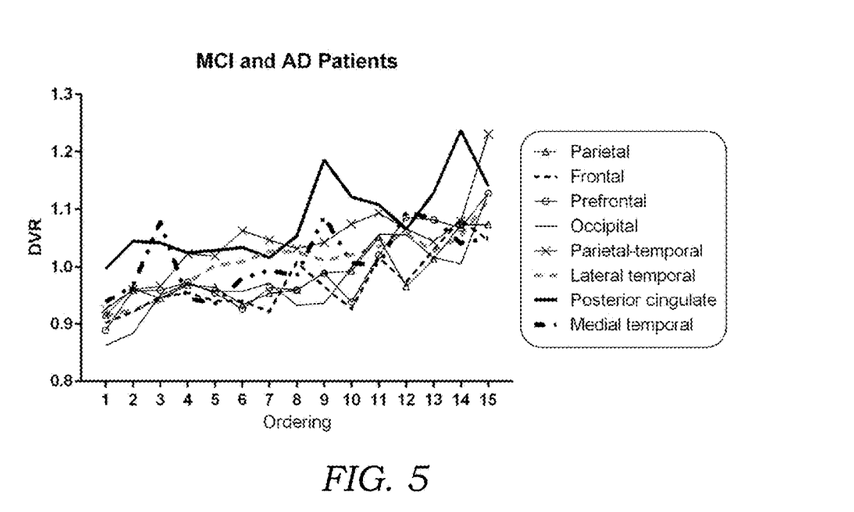
FIG. 5 illustrates the typical trends of [F-18]FDDNP binding (in terms of distribution volume ratio, DVR) in the different cortical regions as a function of the order determined by permuting all fifteen (15) subjects.

FIG. 5 illustrates the typical trends of [F-18]FDDNP binding (in terms of distribution volume ratio, DVR) in the different cortical regions as a function of the order determined by permuting all fifteen (15) subjects using the simulated annealing algorithm so that the total changes of binding and perfusion in the included regions between adjacent subjects are minimized. More advanced disease stage is reflected by a higher position in the ordering (i.e., toward the right hand side of the abscissa). The same results were obtained with the "brute force" permutation generation method, which required much longer computational time (22 hours) than the simulated annealing approach (~30 seconds).

Figure 6A:
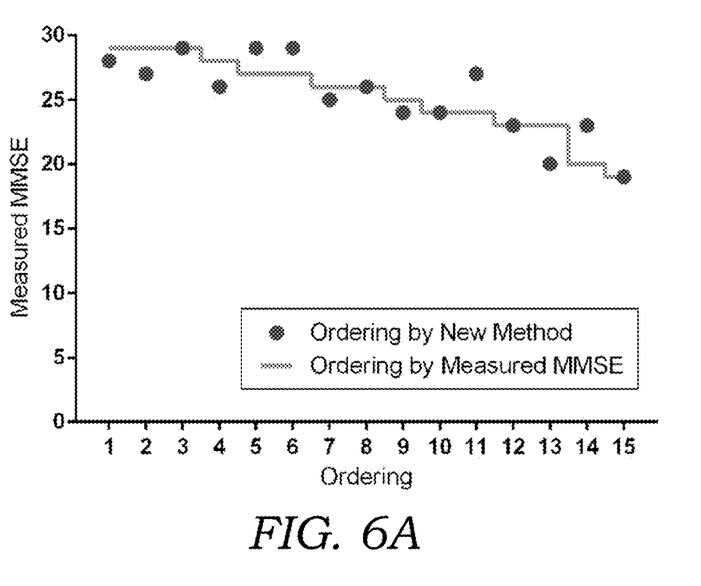
FIG. 6A illustrates a graph showing the ordering by the new method vs. the ordering by the measured MMSE scores.
Figure 6B:
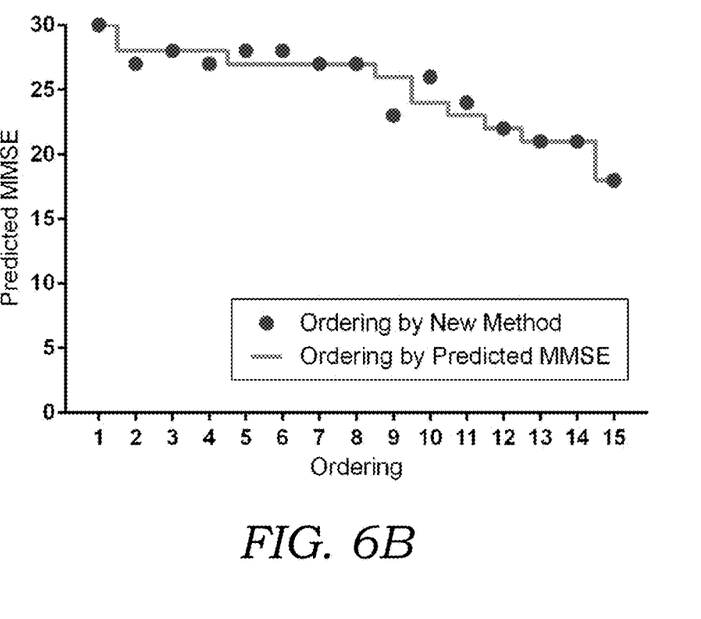
FIG. 6B illustrates a graph showing the ordering by the new method vs. the ordering by the predicted MMSE scores. The new method provided orderings that closely followed those based on the measured and predicted MMSE.

FIG. 6A illustrates a graph showing the ordering of the fifteen (15) subjects by the ordering method described herein vs. the ordering by the measured MMSE scores. FIG. 6B illustrates a graph showing the ordering of the fifteen (15) subjects by the ordering method described herein vs. the ordering by the predicted MMSE scores. The inventive method of ordering provided orderings that closely followed those based on the measured and predicted MMSE.

Figure 7A:
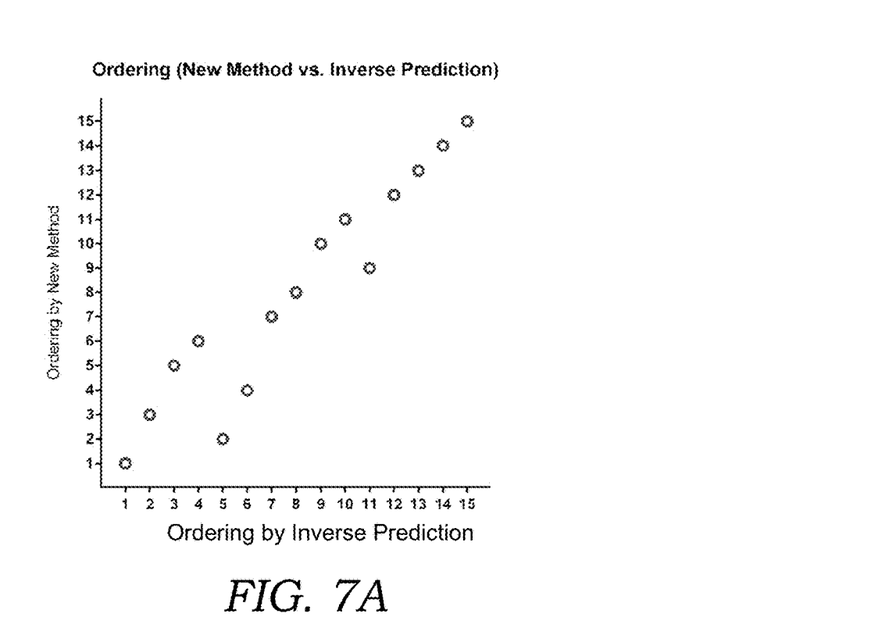
FIG. 7A illustrates a graph showing the correspondence between the orderings determined by the new method and the inverse prediction method based on the measured MMSE scores (Spearman correlation, $r_s$=0.95, P<0.0001).
Figure 7B:
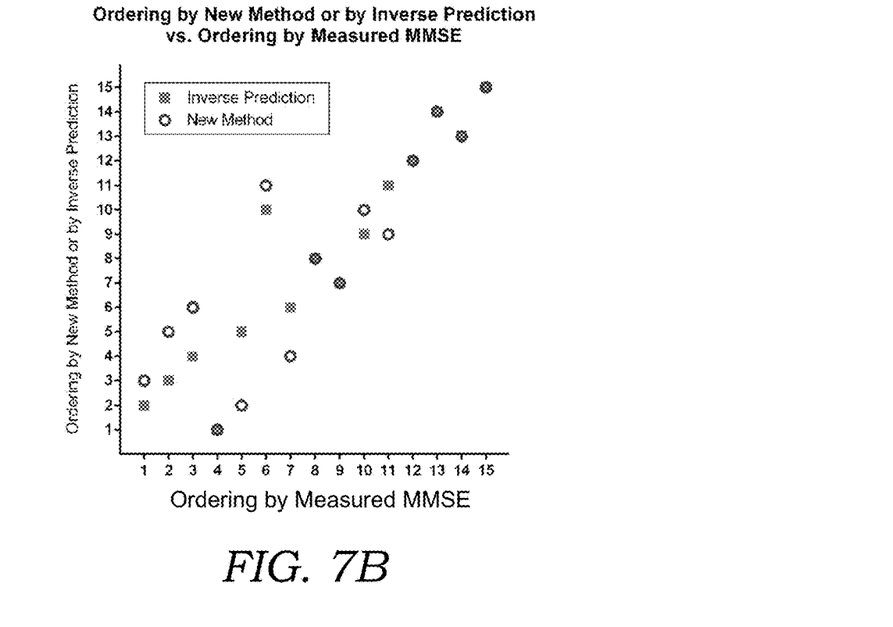
FIG. 7B illustrates a graph illustrating the comparison of the ordering determined by the measured MMSE scores to the orderings obtained with the inverse prediction method[2] ($r_s$=0.93, P<0.0001) and the new method ($r_s$=0.85, P<0.0001)

FIG. 7A illustrates a graph showing the correspondence between the orderings determined by the ordering method described herein and the inverse prediction method of Protas et al. based on the measured MMSE scores (Spearman correlation, $r_s$=0.95, P<0.0001). FIG. 7B shows a graph illustrating the comparison of the ordering determined by the measured MMSE scores to the orderings obtained with the inverse prediction method ($r_s$=0.93, P<0.0001) and the new method ($r_s$=0.85, P<0.0001).

Figure 8:
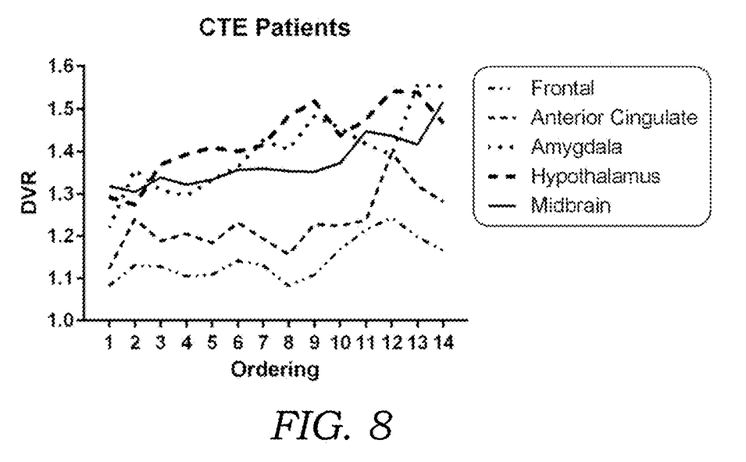
FIG. 8 illustrates the progressive course (DVR values) of fourteen (14) suspected CTE patients for five (5) different brain regions, including frontal, anterior cingulate, amygdala, hypothalamus, and midbrain. This also illustrates that the regions to be used for calculating the cost and thus for determining different neurological diseases could be different.

The permutation or ordering method described herein has also been applied to a small set of fourteen (14) suspected CTE patients. For these experiments, the ROIs that were looked at for DVR values included the following brain regions: frontal, anterior cingulate, amygdala, hypothalamus, midbrain. The progressive courses of the various brain regions critically involved in CTE and obtained from this application are shown in FIG. 8. FIG. 9 shows the typical [F-18]FDDNP DVR images at four (4) stages (T1 (early), T2, T3, T4 (advanced)) of CTE.

While the embodiments and experimental results described herein utilized dynamic PET scans, in some other embodiments, it may be possible to use a single, static PET scan or a summation of multiple time frames acquired over a short time window. For example, it has been found that the 45-55 min (i.e., a 10-min static PET scan) standardized uptake value ratio (SUVR) is practical for quantification of [F-18]FDDNP PET studies. Thus, a single or static PET scan could be used as an alternative to dynamic PET scans. In such an embodiment, one or more SUVR images obtained over a short time window between the start of the scan (time=0) and the end of the scan (e.g., 60-120 minutes) could be used to replace the DVR images obtained with a dynamic scan. This may include a single image or multiple images (e.g., a summed image) obtained within a short time segment/window during the PET scan (e.g., summed image from 35-45 minutes).

The methods described herein may be used to monitor the severity of the subject's neurodegenerative state over time.

For example, the subject 12 may undergo periodic PET studies to evaluate whether or not the neurodegenerative disease has advanced or stabilized. Such studies may be conducted after several weeks, months, or years have elapsed so the subject's condition may be monitored. Such studies may be done in conjunction with the administration of therapeutics or drugs which are administered to the subject 12.

While embodiments of the present invention have been shown and described, various modifications may be made without departing from the scope of the present invention. The invention, therefore, should not be limited, except to the following claims, and their equivalents.

What is claimed is:

1. A method of characterizing a neurodegenerative disease in a subject using positron emission tomography (PET) comprising:
   obtaining a magnetic resonance image of the subject's brain;
   obtaining in vivo PET images of the subject's brain after a radioactive tracer is administered to the subject;
   mapping the PET images to a common space using the magnetic resonance image;
   generating distribution volume ratio (DVR) images of the subject's brain and mapping the same images onto the common space, wherein the DVR images comprise a plurality of different brain regions, each region defining a different region of interest (ROI);
   extracting DVR values for the ROIs of the subject;
   providing a computer accessible database containing DVR values for the population of subjects with the neurodegenerative disease at different stages obtained with in vivo PET images using the radiotracer;
   using the DVR values of the different regions of interest (ROI) of the subject to order the subject among the population of subjects by minimizing a total distance measure as represented by: $\Sigma_{i=1}^{m-1}\Sigma_{j=1}^{n}|ROI_{i,j}-ROI_{i+1,j}|$, where $ROI_{i,j}$ is the DVR value at structural region j of an $i^{th}$ subject, n is the number of structural regions, and m is the number of total subjects; and
   characterizing the neurodegenerative disease for the subject based on the ordering of the subject in the population of subjects.

2. The method of claim 1, wherein the method of ordering the subject among the population is performed by software executed on at least one processor and configured to order the subject among the population of subjects using one of: pairwise interchange, simple local search (2-Opt) heuristic, and a simulated annealing algorithm.

3. The method of claim 1, wherein the method of ordering the subject among the population is performed by software executed on at least one processor and configured to order the subject among the population of subjects using a fast permutation generation method to generate all possible orderings and an ordering with the shortest total distance is selected.

4. The method of claim 1, wherein the neurodegenerative disease comprises Alzheimer's disease (AD).

5. The method of claim 1, wherein the neurodegenerative disease comprises Mild Cognitive Impairment (MCI).

6. The method of claim 1, wherein the neurodegenerative disease comprises Chronic Traumatic Encephalopathy (CTE).

7. The method of claim 1, wherein the number of structural regions (n) is ≤8.

8. The method of claim 1, wherein the number of structural regions comprises one or more of: the parietal region, the frontal region, the prefrontal region, the occipital region, the parietal-temporal border, the lateral temporal region, the posterior cingulate region, and the medial temporal region.

9. The method of claim 1, wherein the number of structural regions comprises one or more of: the frontal region, the anterior cingulate region, amygdala region, hypothalamus region, and the midbrain region.

10. The method of claim 1, wherein the computer accessible database further contains perfusion ROI values for the population of subjects and wherein the method further includes extracting a perfusion value for a ROI of the subject and wherein $ROI_{i,j}$ is the DVR and/or perfusion ROI value at structural region j of an $i^{th}$ subject.

11. A method of characterizing neurodegenerative disease in a subject using positron emission tomography (PET) comprising:
providing a computer accessible database containing region of interest (ROI) images or ROI values of a population of subjects with the neurodegenerative disease at different stages obtained with in vivo PET images using a radiotracer;
obtaining a magnetic resonance image of the subject's brain;
obtaining in vivo PET images of the subject's brain after the radioactive tracer is administered to the subject;
mapping the PET images to a common space using the magnetic resonance image;
generating distribution volume ratio (DVR) images of the subject's brain and mapping the same image onto the common space, wherein the DVR images comprise a plurality of different brain regions, each region defining a different ROI;
extracting DVR values for each different ROI for the subject; and
executing a software algorithm on a computer that uses the DVR values of each different ROI to order the subject among the population of subjects by minimizing a total distance measure as represented by: $\Sigma_{i=1}^{m-1}\Sigma_{j=1}^{n}|ROI_{i,j}-ROI_{i+1,j}|$, where $ROI_{i,j}$ is the image value at structural region j of an $i^{th}$ subject, n is the number of structural regions, and m is the number of total subjects; and
characterizing the stage or severity of the neurodegenerative disease for the subject based on the ordering.

12. The method of claim 11, wherein characterizing the stage or severity comprises identifying the stage or severity based upon a known stage or severity of an adjacent subject in the ordered subjects.

13. The method of claim 12, wherein the software algorithm orders the subject using an insertion method among the population of subjects.

14. The method of claim 11, wherein the method of ordering the subject among the population is performed by software executed on at least one processor and configured to order the subject among the population of subjects using one of: pairwise interchange, simple local search (2-Opt) heuristic, and a simulated annealing algorithm.

15. The method of claim 11, wherein the database contains perfusion ROI values for the population of subjects and wherein the method further includes extracting a perfusion value for a ROI of the subject and wherein the software algorithm uses the perfusion value for the ROI as well as the DVR values to order the subject among the population of subjects by minimizing the total distance measure.

16. The method of claim 15, wherein the neurodegenerative disease comprises Alzheimer's disease (AD).

17. The method of claim 15, wherein the neurodegenerative disease comprises Mild Cognitive Impairment (MCI).

18. The method of claim 11, wherein the neurodegenerative disease comprises Chronic Traumatic Encephalopathy (CTE).

19. A method of diagnosing neurodegenerative disease in a subject using positron emission tomography (PET) comprising:
providing a computer accessible database containing brain region specific distribution volume ratio (DVR) values and/or perfusion values of a first population of subjects with Alzheimer's disease (AD) and a second population of subjects with Chronic Traumatic Encephalopathy (CTE) obtained using a radiotracer, wherein the first population of subjects and the second population of subjects are ordered according to their disease state progression;
obtaining a magnetic resonance image of the subject's brain;
obtaining in vivo dynamic PET images of the subject's brain after the radioactive tracer is administered to the subject;
registering the dynamic PET images with the magnetic resonance image of the subject's brain onto the common space;
extracting brain region specific DVR values and/or perfusion values of the subject;
comparing the brain region specific extracted DVR values and/or perfusion values of the subject to the brain region specific DVR values and/or perfusion values stored in the database of the first population of subjects and the second population of subjects, wherein the comparison involves software computing a distance between the DVR values and/or perfusion values of the subject and the DVR and/or perfusion values of the first population and the second population; and
diagnosing the neurodegenerative disease as either AD or CTE for the subject based on the computed distance.

20. The method of claim 19, wherein the diagnosing is made based on the lowest computed distance.

21. The method of claim 19, wherein the computation involves a summation of the differences between brain region specific DVR values and/or perfusion values of the subject and the brain region specific DVR values and/or perfusion values of the first population and the second population.

22. A method of characterizing neurodegenerative disease in a subject using positron emission tomography (PET) comprising:
providing a computer accessible database containing region of interest (ROI) images or ROI values of a population of subjects with the neurodegenerative disease at different stages obtained with in vivo static PET images using a radiotracer;
obtaining a magnetic resonance image of the subject's brain;
obtaining in vivo static PET images of the subject's brain after the radioactive tracer is administered to the subject;
mapping the PET images to a common space using the magnetic resonance image;
generating standardized uptake value ratio (SUVR) images of the subject's brain and mapping the same image onto the common space, wherein the SUVR images comprise a plurality of different brain regions, each region defining a different ROI;

extracting SUVR values for each different ROI for the subject; and executing a software algorithm on a computer that uses the SUVR values of each different ROI to order the subject among the population of subjects by minimizing a total distance measure as represented by: $\Sigma_{i=1}^{m-1}\Sigma_{j=1}^{n}|ROI_{i,j}-ROI_{i+1,j}|$, where $ROI_{i,j}$ is the image value at structural region j of an $i^{th}$ subject, n is the number of structural regions, and m is the number of total subjects; and characterizing the stage or severity of the neurodegenerative disease for the subject based on the ordering.

* * * * *